Figure 1:
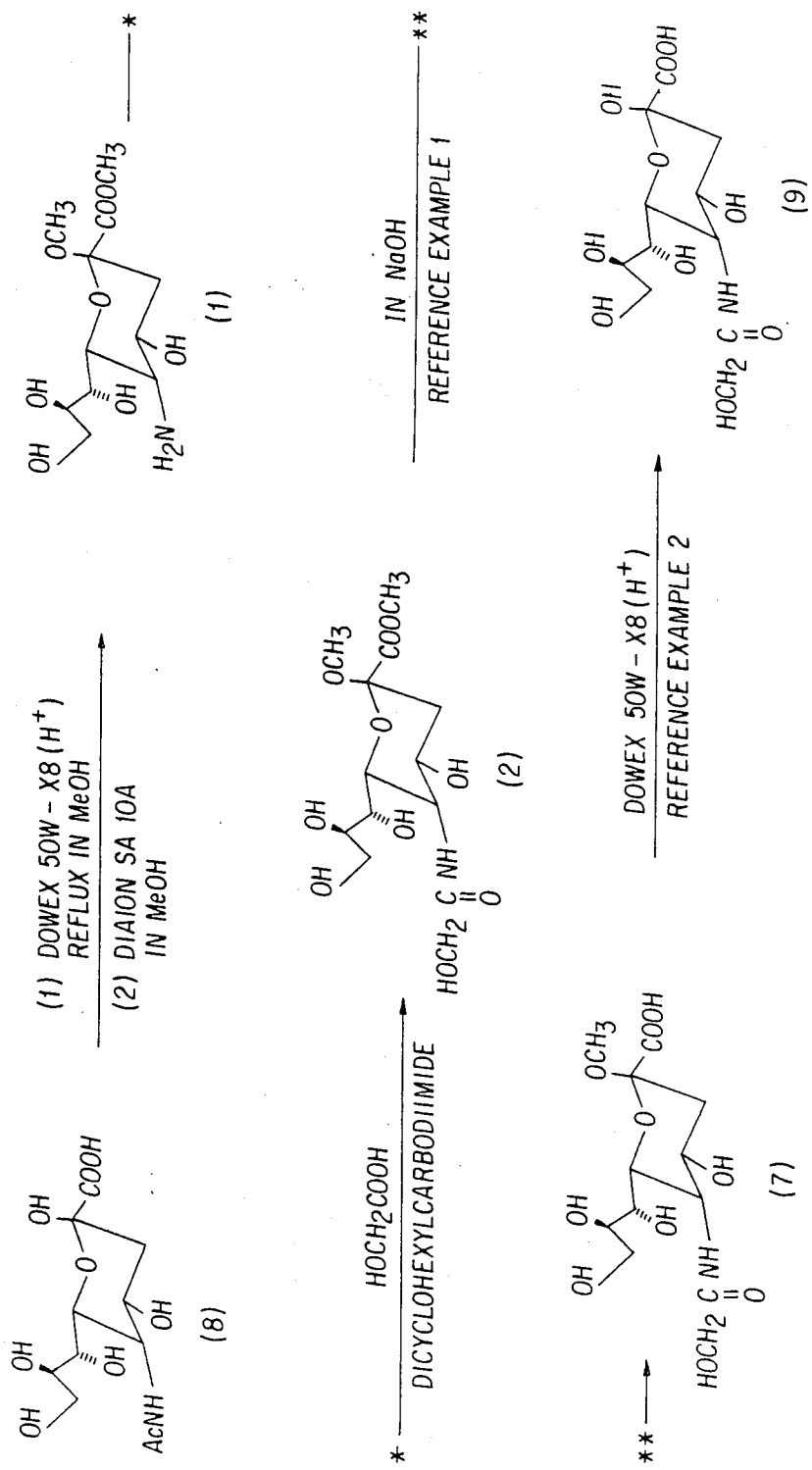

United States Patent [19]

Shibayama et al.

[11] Patent Number: 4,774,326
[45] Date of Patent: Sep. 27, 1988

[54] PROCESS FOR PREPARING N-GLYCOLYLNEURAMINIC ACID DERIVATIVES

[75] Inventors: Shohei Shibayama; Shoji Yoshimura, both of Saitama; Masayoshi Ito, Tokyo; Yoshiyasu Shitori, Tokyo; Tomoya Ogawa, Tokyo, all of Japan

[73] Assignee: Mect Corporation, Tokyo, Japan

[21] Appl. No.: 917,538

[22] Filed: Oct. 10, 1986

[30] Foreign Application Priority Data

Oct. 11, 1985 [JP] Japan .................. 60-226540
Oct. 6, 1986 [JP] Japan .................. 61-237766

[51] Int. Cl.$^4$ ............ C07H 15/04; C07H 13/04; C07B 59/00
[52] U.S. Cl. .................. 536/18.5; 536/4.1; 536/17.2; 536/18.2; 536/18.7; 536/53; 536/55.3; 536/124
[58] Field of Search ............ 536/4.1, 17.2, 18.2, 536/18.5, 18.7, 55.3, 124, 18.4, 53

[56] References Cited

U.S. PATENT DOCUMENTS

| | | | |
|---|---|---|---|
| 4,593,091 | 6/1986 | Della Valle et al. | 536/55.1 |
| 4,663,443 | 5/1987 | Shibayama et al. | 536/18.2 |
| 4,675,391 | 6/1987 | Shibayama et al. | 536/18.4 |
| 4,691,012 | 9/1987 | Ogura et al. | 536/55.3 |
| 4,694,076 | 9/1987 | Ogawa et al | 536/4.1 |

FOREIGN PATENT DOCUMENTS 86114034 7/1987 European Pat. Off. .
2101588 1/1983 United Kingdom .................. 536/53

OTHER PUBLICATIONS

H. Faillared, Angew. Chem. Internat. Edit vol. 4 445–46 Angew. Chem., 77, 431 (1965).
Hans Faillard, Hoppe-Seyler's Z. Physiol. Chem., 341, 167–171 (1965).
Wolfgang Wesemann, Ann. Chem. 695, 209 (1966).
Von Ferdinand et al., Hoppe-Seyler's Z. Physiol. Chem., 350, 111–115 (1969).
Roland Schauer, Hoppe-Seyler's Z. Physiol. Chem., 351, 359 (1970).
Michael F. Czarneiecki, J.A.C.S., 99, 8273 (1977).
P. Meindl et al., Monatsh, Chem. 97, 654 (1966).
P. Meindl et al., Monatsh, Chem. 100, 1295–1306 (1969).

*Primary Examiner*—Ronald W. Griffin
*Assistant Examiner*—Nancy S. Carson
*Attorney, Agent, or Firm*—Oblon, Fisher, Spivak, McClelland & Maier

[57] ABSTRACT

This invention provides a novel process for preparing a compound represented by the formula

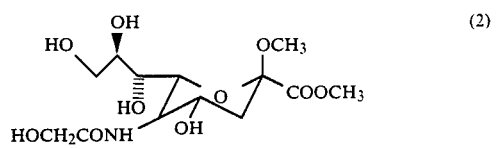
(2)

In accordance with this invention, the compound is prepared by reacting a compound represented by the formula

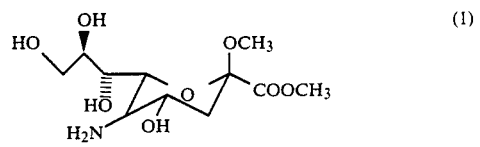
(1)

with glycolic acid in the presence of dicyclohexylcarbodiimide. The compound (2) is a useful precursor for the preparation of N-glycolylneuraminic acid:

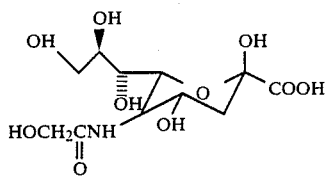

6 Claims, 2 Drawing Sheets

PROCESS FOR PREPARING N-GLYCOLYLNEURAMINIC ACID DERIVATIVES

BACKGROUND OF THE INVENTION (1) Field of the Invention

The present invention relates to a novel process for preparing N-glycolylneuraminic acid, particularly to a novel process for preparing N-glycolylneuraminic acid derivatives, precursors of N-glycolylneuraminic acid, from neuraminic acid derivatives and glycolic acid. N-glycolylneuraminic acid has recently drawn attention as a tumor-associated antigen and as a subject of embryological research.

(2) Description of the Prior Art

The process proposed by Schauer et al, Hoppe-Seyler's, Z.Physiol.Chem., vol. 351, 359–364 (1970), is known as a process for preparing an N-glycolylneuraminic acid derivative, which is a precursor for preparing N-glycolylneuraminic acid, from a neuraminic acid derivative and glycolic acid. In this process, dioxolandione (5) is obtained from glycolic acid (3) and phosgene (4), and then the dioxolandione (5) is reacted with a neuraminic acid derivative (6).

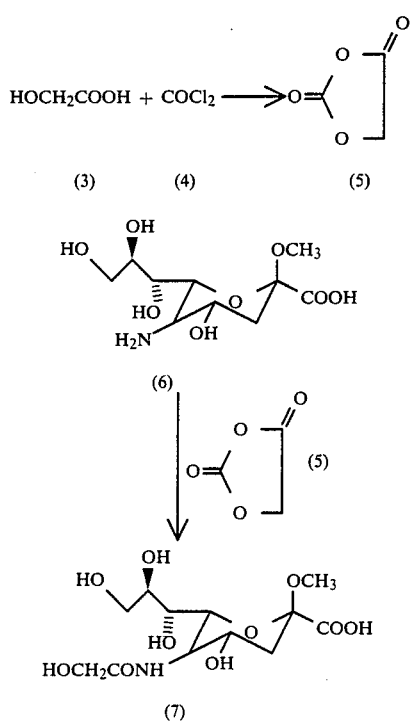

However this process has the following disadvantages:

Phosgene has to be used for the synthesis of dioxolandione (5) but it has strong toxicity and the handling thereof involves some risk;

Two steps are required for the reaction process; and

The yield of a N-glycolylneuraminic acid derivative, the object compound, is low (23%).

Hitherto, no process for preparing N-glycolylneuraminic acid derivatives by directly reacting neuraminic acid derivatives with glycolic acid has been known.

SUMMARY OF THE INVENTION

The object of the present invention is to provide a process for preparing N-glycolylneuraminic acid derivatives which uses a compound which can be handled safely as a raw material (which does not require difficult-to-handle phosgene), which comprises a single step and which provides the object compound at a high yield.

According to the present invention, a novel process for preparing the compound represented by the formula (2)

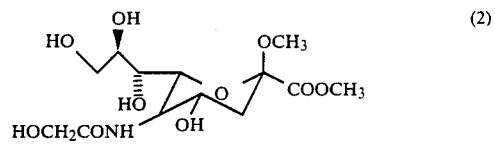

characterized in reacting the compound represented by the formula (1)

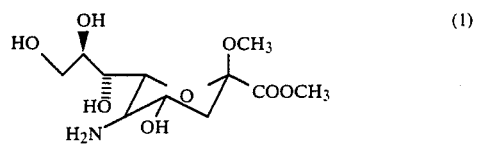

with glycolic acid in the presence of dicyclohexylcarbodiimide.

Figure 2:
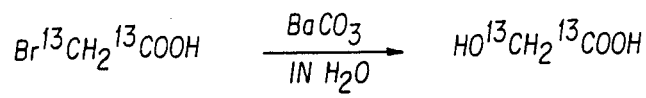
Figure 2:
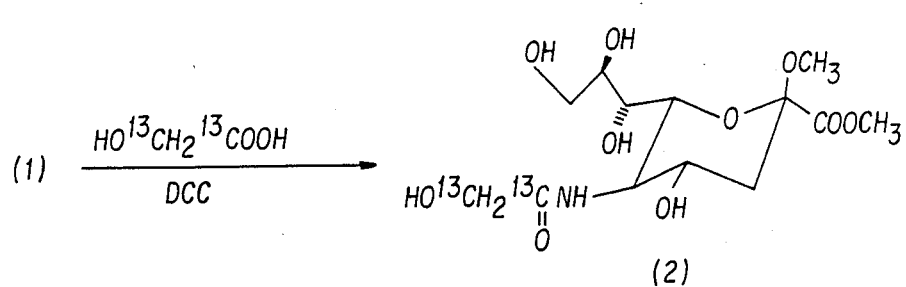
Figure 2:
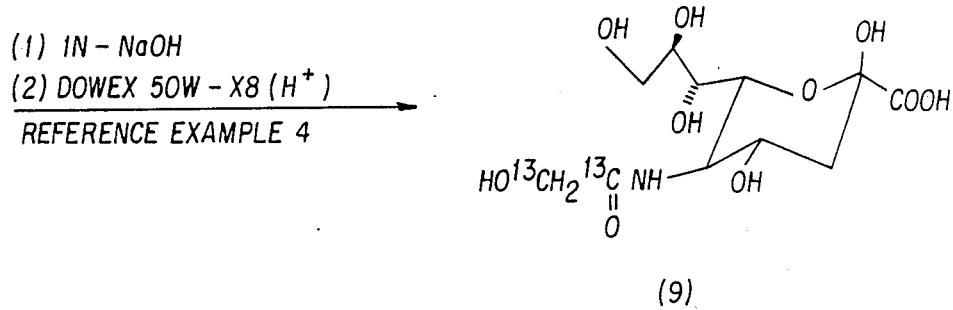

The process of the present invention will be illustrated as follows. The present invention and the steps of the process from N-glycolylneuraminic acid derivative (2) and (2') produced by the present invention to N-glycolylneuraminic acid (9) and (9') are shown in FIGS. 1 and 2.

FIG. 1

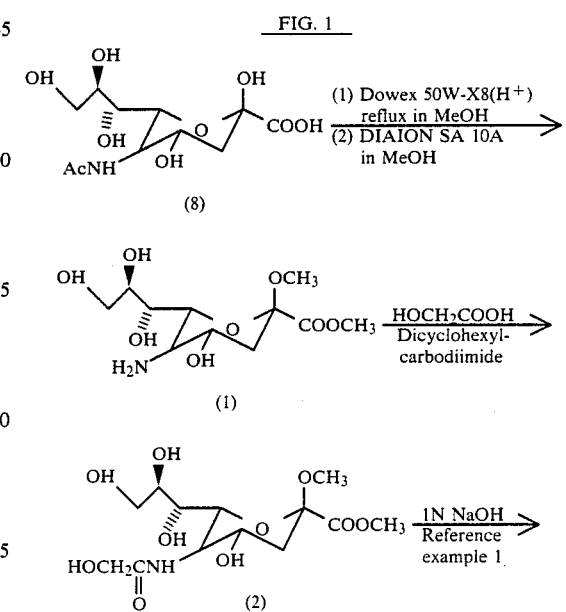

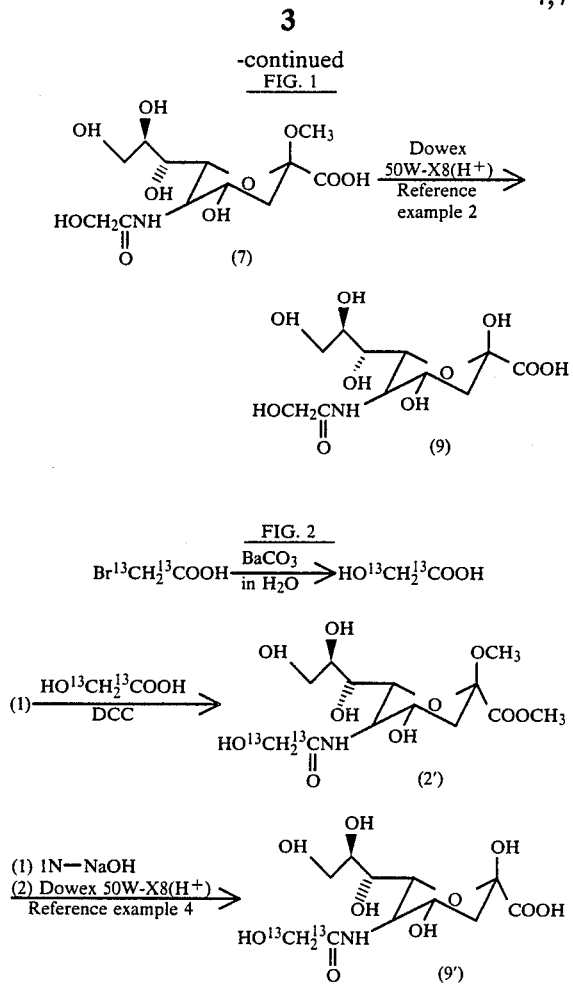

FIG. 1 (continued) / FIG. 2

Methyl 2-0-methyl-β-D-neuraminate (1), which is a raw material of the present invention and a publicly known compound, is quantitatively prepared by a conventional method from N-acetylneuraminic acid (8) which is commercially available and can be obtained easily. A typical conventional method of this type is one in which N-acetyl neuraminate (8) is refluxed in the presence of Dowex 50W-X8(H+) or the like in methanol and then the resulting compound is eluted with a solvent of HCl—MeOH from the Dowex resin followed by neutralization.

Glycolic acid, which is another raw material, is commercially available and can be obtained easily.

In the present invention, HO$^{13}$CH$_2^{13}$COOH((1,2-$^{13}$C$_2$) glycolic acid) containing $^{13}$C, an isotope of carbon, may be also used as glycolic acid (see flowsheet 2). Such glycolic acid can be obtained by reacting bromoacetic acid (Br$^{13}$CH$_2^{13}$COOH) and BaCO$_3$ in water. Bromoacetic acid is commercially available and can be obtained easily.

The preparation method of this invention is usually carried out in a solvent. Usable solvents include methylene chloride, acetonitrile, N,N'-dimethylformamide (DMF), pyridine, tetrahydrofuran and the like, and pyridine and DMF are especially preferred.

Although the reaction can be carried out by stirring the reaction mixture at room temperature, it is preferred that dicyclohexylcarbodiimide (hereinafter DCC) be added to a mixture of compound (1) and glycolic acid while keeping the reaction mixture at −10° C. to 25° C. (preferably 0° to 5° C.), followed by the agitation at the same temperature as above and the agitation at room temperature. This is because such condition tends to make yield of the reaction higher. From the viewpoint of economy and yield, the mixing mole ratio of compound (1): HOCH$_2$COOH: DCC preferably ranges between 1:about 1 to 1.5:about 1 to 1.5, from a practical point of view, more preferably 1:1:1.3.

In the present invention, in order to obtain the objective compound at high yield, it is preferred that N-hydroxy-5-norbornene-2,3-dicarboximide (hereinafter HONB) and N-ethylmorpholine be present in the reaction mixture in addition to DCC. The ratio of HONB and N-ethylmorpholine used in the reaction to compound (1) range respectively between about 1:1 to 1.5:1. In this reaction, the use of DMF as a solvent is especially preferred. The preferred reaction procedure is as follows: a DMF solution containing compound (1), glycolic acid, HONB and N-ethylmorpholine is added with DCC under cooling and stirred for about 1 to 3 hours, followed by agitation at room temperature. N-hydroxy compounds such as N-hydroxysuccinimide (HOSu), 1-hydroxybenzotriazole (HOBt), 3-hydroxy-4-oxo-3,4-dihydro-1,2,3-benzotriazine (HOOBt) and the like may be used.

The present invention relates to a process for preparing compound (2) which is a precursor of N-glycolylneuraminic acid (9). This N-glycolyl neuraminic acid (9) is an important compound in cancer and embryological research. For example, both N-glycolyl- and N-acetyl-sialic acids are found in intestines, cells and humors of various animals. However, N-glycolyl-sialic acid is not present in man and domestic fowls. It is considered that this difference in the distribution of sialic acid among species of animals has some immunological significance. For example, if tissue or blood serum of other animals enters the human body, an antibody is produced to a determinant containing N-glycolyl neuraminic acid, one kind of N-glycolyl-sialic acid and a serum discase type antibody (H-D antibody) is actually known as such antibody. From such immunological knowledge and the fact that the H-D antibody locates on the cancer cell surface at a high rate, N-glycolyl neuraminic acid is noted to be an antigen determinant of a tumor-associated antigen.

On the other hand, Yamakawa et al, J. Biochem., 83, 1101 (1978) report a case of embryological interest relative to the difference in the distribution of N-acetly- and N-glycolyl-sialic acids. That is, European dogs such as the Beagle and dogs from the northern part of Japan such as the Akita dog have only N-acetyl-sialic acid. However, Japanese dogs (dogs indigenous to Japan) such as the Shiba dog generally have only N-acetyl-sialic acid but some Japanese dogs having N-acetyl and N-glycolyl-sialic acid were also found.

For example, as shown in the flowsheets 1 and 2, N-glycolylneuraminic acid (9), which is a compound with very interesting properties as noted above, can be prepared from compound (2) obtained by the process of the present invention as a raw material as follows. Compound (2) is treated with an alkali aqueous solution to produce compound (7) and then the compound (7) is treated with Dowex 50W-X8(H+) in acid solution. Whereupon N-glycolylneuraminic acid (9) is obtained.

In the present invention, as shown in the flowsheet 2, when HO$^{13}$CH$_2^{13}$COOH containing $^{13}$C is used as glycolic acid, compound (2') containing $^{13}$C can be obtained. N-glycolylneuraminic acid (9') containing $^{13}$C can be obtained by treating compound (2') under the same conditions as in the treatment of compound (2). Compound (9') containing $^{13}C$ is a useful labeled compound for investigation of the intravital metabolism mechanism. That is, the compound containing $^{13}C$ can be used as a non-radioactive labeled compound, which can easily be detected by nuclear magnetic resonance or mass spectrography, for the detection of the intravital metabolism products, the distribution thereof and metabolism mechanism research without special experimental apparatus.

The present invention will now be illustrated by referring to the following nonlimitative examples.

EXAMPLE 1

13.86 g (46.937 m mol) methyl (methyl 5-amino-3,5-dideoxy-β-D-glycero-D-galacto-2-nonylpyranoside)onate (compound 1) was dissolved in 300 ml DMF and then added with 3.57 g (46.937 m mol) glycolic acid, 10.93 g (61.018 m mol) HONB (N-hydroxy-5-norbornane-2,3-dicarboxyimide) and 5.54 ml (46.936 m mol) N-ethylmorpholine. Then the resulting reaction solution was added with 12.59 g (61.018 m mol) DCC under cooling and stirred for 3 hours, followed by agitation at room temperature for 48 hours. The resulting reaction suspension was filtrated and the resulting filtrate was concentrated to dryness. The thus obtained residue was subjected to silica gel column chromatography and fractionated by a mixed solvent of chloroform:methanol:acetic acid=6:3:0.2 to obtain compound (2) as a colorless amorphous crystal (14.09 g, 85%).

| Decomposition point: | 92–98° C. |
|---|---|
| $[\alpha]_D^{20}$ −27.5° | (C = 1, $H_2O$) |
| Elemental analysis | $C_{13}H_{23}NO_{10} \cdot 1/5H_2O$ |
| | MW = 400.18 |
| Calculation | C: 39.02 H: 7.10 N: 3.50 |
| Found | C: 39.08 H: 6.70 N: 3.51 |
| $IR\nu_{max}^{KBr}$ cm$^{-1}$ | 3400 (—OH, —NH—) |
| | 1740 (—$COOCH_3$) |
| | 1650 (—CONH—) |
| | 1550 (—CONH, amide II) |
| $^1H$—NMR$_{400\ MHz}^{ppm}$ | ($D_2O$, t-BuOH) |
| | 1.811 (1H, dd, J = 13.2 Hz, J = 11.4 Hz, Hax-3) |
| | 2.413 (1H, dd, J = 13.2 Hz, J = 5.1 Hz, Heq-3) |
| | 3.291 (3H, s, $CH_3O$—2) |
| | 3.881 (3H, s, —$COOCH_3$) |
| | 4.147 (2H, s, HOC$H_2$CO—) |
| $^{13}C$—NMR$_{100\ MHz}^{ppm}$ | ($D_2O$, t-BuOH) |
| | 39.879 (C-3) |
| | 51.687 ($CH_3O$—2) |
| | 52.121 (C-5) |
| | 54.178 (—COO$CH_3$) |
| | 61.719 (HO$CH_2$CONH—) |
| | 64.028 (C-9) |
| | 66.812 (C-4) |
| | 68.771 (C-7) |
| | 70.646 (C-6) |
| | 71.066 (C-8) |
| | 99.902 (C-2) |
| | 171.008 (—$C$ONH—) |
| | 176.198 (—$C$OOCH$_3$) |

EXAMPLE 2

1 g (3.39 m mol) compound (1), 258 mg (3.39 m mol) glycolic acid and 909 mg (4.407 m mol) DCC were dissolved in 100 ml pyridine under cooling condition, followed by agitation at room temperature for 48 hours. The resulting suspension was filtrated and the filtrate thus obtained was concentrated to dryness. The resulting residue was subjected to silica gel column chromatography and fractionated by a mixed solvent of chloroform:methanol:acetic acid=6:3:0.2 to obtain compound (2) as a colorless amorphous crystal (840 mg, 70%).

EXAMPLE 3

In accordance with the precedure of example 2 but using DMF in place of pyridine, compound (2) was obtained (450 mg, 38%).

REFERENCE EXAMPLE 1

Preparation of methyl 5-N-glycolyl-3,5-dideoxy-β-D-glycero-D-galacto-2-nonulopyranosidonic acid (7)

200 mg methyl(methyl 5-N-acetoxyacetyl-3,5-dideoxy-4,7,8,9-tetra-0-acetyl-β-D-glycero-D-galacto-2-nonulopyranosid)onate was added with 5 ml purified water and 2.2 ml 1N-sodium hydroxide and stirred at room temperature for 3 hours. The reaction mixture was neutralized with Dowex 50W-X8(H+) and freeze-dried to obtain the captioned compound as an amorphous (96 mg, 80%).

| $IR\nu_{max}^{KBr}$ cm$^{-1}$ | 3400 (—OH, —NH—) |
|---|---|
| | 1730 (—COOH) |
| | 1650 (—CONH—) |
| | 1550 (—CONH, amide II) |

REFERENCE EXAMPLE 2

Preparation of N-glycolylneuraminic acid (9)

0.86 g (2.434 m mol) methyl(methyl 5-N-glycolyl-3,5-dideoxy-β-D-glycero-D-galacto-2-nonulopyranoside)onate (compound 2) was dissolved in 5 ml purified water and added with 2.5 ml 1N sodium hydroxide aqueous solution. After agitation of the reaction mixture at room temperature for 3 hours, the reaction mixture was acidified with Dowex 50W-X8(H+) and maintained at 80° C. for 3 hours with agitation. The Dowex resin was filtrated and the resulting filtrate was subjected to a Dowex 50W-X8(H+) column (100 ml) and the eluting solution was passed through a Dowex 1×2 (HCOO−) column (110 ml). After 500 ml purified water had flowed therethrough, elution was carried out with 1N-formic acid. Whereupon the captioned compound was obtained from the eluting fractions as a colorless amorphous crystal (600 mg, 76%).

| Decomposition point | 112–124° C. |
|---|---|
| $[\alpha]_D^{27.5}$ −25.33° | (C = 1, $H_2O$) |
| Elemental analysis | $C_{11}H_{19}NO_{10} \cdot 6/5H_2O$ |
| | MW = 346.90 |
| Calculation | C: 38.09 H: 6.22 |
| Found | C: 37.81 H: 6.12 N: 4.51 |
| $IR\nu_{max}^{KBr}$ cm$^{-1}$ | 3420 (—OH, —NH) |
| | 1740 (—COOH) |
| | 1650 (—CONH—) |
| | 1550 (—CONH, amide II) |
| $^1H$—NMR$_{400\ MHz}^{ppm}$ | ($D_2O$, t-BuOH) |
| | 1.811 (1H, dd, J = 13.1 Hz, J = 12.8 Hz, Hax-3) |
| | 2.305 (1H, dd, J = 13.1 Hz, J = 4.9 Hz, Heq-3) |
| | 3.534 (1H, d, J = 9.2 Hz, H-7) |
| | 3.608 (1H, dd, J = 11.9 Hz, J = 6.4 Hz, H-9') |
| | 3.742 (1H, m, H-8) |
| | 3.826 (1H, dd, J = 11.9 Hz, J = 2.8 Hz, H-9) |
| | 4.002 (1H, t, J = 10.4 Hz, H-5) |

| | |
|---|---|
| $^{13}C$—NMR$_{67.7\ MHz}^{ppm}$ | 4.128 (2H, s, HOCH$_2$—CONH—) (D$_2$O, t-BuOH) 39.610 (C-3) 52.506 (C-5) 61.732 (HOCH$_2$CONH—) 63.859 (C-9) 67.713 (C-4) 68.910 (C-7) 70.924 (C-6, 8) 96.051 (C-2) 174.612 (—CONH—) 176.318 (—COOCH$_3$) |
| MS m/z: | 814 (M$^+$—CH$_3$, |
| M$^+$: | C$_{32}$H$_{75}$NO$_{10}$Si$_7$ = 829) |

The obtained colorless amorphous crystal (compound 9) was recrystallized from water-acetic acid (1:4) and colorless needles were obtained.
Decomposition point 173° C.

REFERENCE EXAMPLE 3

Preparation of (1,2-$^{13}C_2$) glycolic acid 2 g (14.1854 m mol) bromo (1,2-$^{13}C_2$) acetic acid was dissolved in 20 ml purified water and added with 5.6 g (28.3708 m mol) barium carbonate, followed by refluxing for 35 hours with agitation. After the filtration of the reaction mixture, the resulting filtrate was added with 1.42 g sulfuric acid and the precipitated compound was removed by filtration. The thus obtained filtrate was added with amberlite IRA-94 and adjusted to pH 2.7. After the filtration of the amberlite, the obtained filtrate was passed through a Dowex 50W-X8(H+) column (2×20 cm) and elution was carried out by purified water. The resulting eluting solution was freeze-dried to obtain the captioned compound (660 mg, 60%).

IR$\nu_{max}^{KBr}$ cm$^{-1}$: 3400 (—OH), 1690 ($^{13}$COOH)

EXAMPLE 3

Preparation of methyl(methyl 5-N-(1,2-$^{13}C_2$) glycolyl-3,5-dideoxy-β-D-glycero-D-galacto-2-nonulopyranoside)oate (2')

2.62 g (8.8616 m mol) methyl (methyl 5-amino-3,5-dideoxy-β-D-glycero-D-galacto-2-nonulopyranosid)onate (1) and 451 mg (7.3845 m mol) (1,2-$^{13}C_2$) glycolic acid obtained in Reference example 3 were dissolved in 70 ml anhydrous DMF and added with 1.05 ml N-ethylmorpholine and 1.72 g (9.5999 m mol) HONB (N-hydroxy-5-norbornene-2,3-dicarboximide). Then 1.98 g (9.5999 m mol) was added to the reaction mixture and stirred for 2 hours under cooling, followed by agitation at room temperature for 48 hours. The resulting reaction suspension was filtrated and thus obtained filtrate was concentrated to dryness. The obtained residue was subjected to silica gel column chromatography and fractionated by a solvent of chloroform:methanol:ethyl acetate = 10:5:1 to obtain a colorless amorphous crystal (1.64 g, 80%). The resulting colorless amorphous crystal was recrystallized from methanol, whereupon compound (2') was obtained as colorless needles.

| | |
|---|---|
| Decomposition point: | 199–200° C. |
| Elemental analysis | (C$_{11}$H$_2$NO$_{10}$ + $^{13}$C$_2$).H$_2$O = 373.33 |

| | |
|---|---|
| Calculation | C: 42.35 H: 6.75 N: 3.75 |
| Found | C: 42.24 H: 6.46 N: 3.70 |
| IR$\nu_{max}^{KBr}$ cm$^{-1}$ | 3400 (—OH, —NH) 1740 (—COOCH$_3$) 1620 (—$^{13}$CONH—) 1530 (—$^{13}$CONH, amide II) |
| $^1$H—NMR$_{400\ MHz}^{ppm}$ | (DMSO—d$_6$ + D$_2$O) 1.539 (1H, dd, J = 13.2 Hz, J = 11.2 Hz, Hax-3) 2.192 (1H, dd, J = 13.2 Hz, J = 4.9 Hz, Heq-3) 3.190 (3H, s, 2-OCH$_3$) 3.413 (1H, dd, J = 11.7 Hz, J = 5.9 Hz, H-9') 3.566–3.752 (4H, m, H-9, H-8, H-5, H-6) 3.714 (3H, s, —COOCH$_3$) 4.011 (1H, dd, J = 11.2 Hz, J = 9.8 Hz, J = 4.9 Hz, H-4) |
| $^{13}$C—NMR$_{100\ MHz}^{ppm}$ | (DMSO—d$_6$ + D$_2$O) 61.184 (d, J = 53.4 Hz, HO$^{13}$CH$_2$—$^{13}$CONH—) 174.26 (d, J = 53.4 Hz, HO$^{13}$CH$_2$—$^{13}$CONH—) |
| POS-FAB-MS m/z: | 356 ((M + 1)$^+$, |
| M: | C$_{11}$H$_{23}$NO$_{10}$ + $^{13}$C$_2$ = 355) |

EXAMPLE 4

1 g (3.39 m mol) compound (1), 172 mg (2.82 m mol) (1,2-$^{13}C_2$) glycolic acid and 909 mg (4.407 m mol) DCC were dissolved in 40 ml pyridine under cooling condition, followed by agitation at room temperature for 48 hours. After the filtration of the thus obtained reaction suspension, the filtrate was concentrated to dryness. The resulting residue was subjected to silica gel column chromatography and fractionated by a mixed solvent of chloroform:methanol:ethyl acetate = 10:5:1. whereupon compound (2') was obtained as a colorless amorphous crystal (577 mg, 48%).

EXAMPLE 5

In accordance with the procedure of Example 4 but using DMF in place of pyridine, compound (2') was obtained (450 mg, 38%).

REFERENCE EXAMPLE 4

Preparation of N-(1,2-$^{13}C_2$) glycolylneuraminic acid (9')

400 mg (1.1258 m mol) methyl(methyl 5-N-(1,2-$^{13}C_2$)glycolyl-3,5-dideoxy-β-D-glycero-D-galacto-2-nonulopyranosid)onate (compound 2') was dissolved in 3 ml purified water and added with 1.4 ml 1N-sodium hydroxide, followed by agitation at room temperature for 3 hours. The resulting reaction mixture was acidified with Dowex 50W-X8(H+) and maintained at 80° C. for 3.5 hours with agitation. The Dowex resin was removed by filtration and filtrate was subjected to a Dowex 50W-X8(H+) column (100 ml). The thus obtained eluting solution was passed through a Dowex 1×2 (HCOO$^-$) column (200 ml) and then 300 ml purified water was passed through the column. Then the elution was carried out by 1N-formic acid and compound (9') was obtained from the resulting fraction solution as a colorless crystal (258 mg, 70%). The obtained colorless crystal (9') was recrystallized from water-acetic acid (1:4) and colorless needles were obained.

| | |
|---|---|
| Decomposition point: | 174–175° C. |
| Elemental analysis | (C$_9$H$_{19}$NO$_{10}$ + $^{13}$C$_2$).½H$_2$O = 336.27 |

| | -continued |
|---|---|
| Calculation | C: 39.88 H: 6.00 N: 4.17 |
| Found | C: 39.95 H: 5.79 N: 4.16 |
| IR$\nu_{max}^{KBr}$ cm$^{-1}$ | 3400 (—OH, —NH) |
| | 1720 (—COOH) |
| | 1625 (—$^{13}$CONH—) |
| | 1515 (—$^{13}$CONH, amide II) |
| $^1$H—NMR$_{400\ MHz}^{ppm}$ | (D$_2$O, acetone) |
| | 1.880 (1H, t, J = 12.7 Hz, Hax-3) |
| | 2.298 (1H, dd, J = 13.2 Hz, J = 4.6 Hz, Heq-3) |
| | 3.534 (1H, d, J = 9.3 Hz, H-7) |
| | 3.615 (1H, dd, J = 11.7 Hz, J = 6.1 Hz, H-9') |
| | 3.752 (1H, ddd, J = 9.3 Hz, J = 6.1 Hz, J = 2.7 Hz, H-8) |
| | 3.834 (1H, dd, J = 11.7 Hz, J = 2.7 Hz, H-9) |
| | 4.005 (2H, ddd, J = 10.9 Hz, J = 10.3 Hz, J = 2.9 Hz, H-5) |
| | 4.133 (2H, dd, J = 145.2 Hz, J = 4.1 Hz, HO$^{13}$CH$_2$$^{13}$CO—) |
| | 4.148 (1H, d, J = 10.9 Hz, H-6) |
| | 4.154 (1H, ddd, J = 12.6 Hz, J = 10.3 Hz, J = 4.6 Hz, H-4) |
| $^{13}$C—NMR$_{22.5\ MHz}^{ppm}$ | (D$_2$O, dioxane) |
| | 176.306 (d, J = 53.7 Hz, HO$^{13}$CH$_2$—$^{13}$CONH—) |
| | 61.820 (d, J = 53.7 Hz, HO$^{13}$$\underline{C}$H$_2$—$^{13}$CONH—) |
| POS-FAB-MS m/z: | 328 ((M + 1)$^+$, |
| M: | C$_9$H$_{19}$NO$_{10}$ + $^{13}$C$_2$ = 327) |
| m/z: | 655 (2M + 1)$^+$ |
| NEG-FAB-MS m/z: | 326 (2M − 1)$^-$ |

We claim:

1. A process for preparing a compound represented by the formula (2)

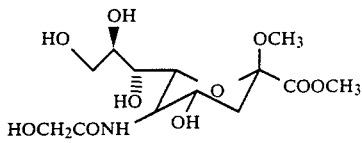

which comprises reacting a compound represented by the formula (1)

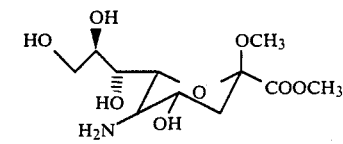

with a glycolic acid in the presence of dicyclohexylcarbodiimide and a solvent, wherein said solvent is selected from the group consisting of methylene chloride, acetonitrile, N,N'-dimethylformamide, pyridine, and tetrahydrofuran, at a temperature of from −10° C. to 25° C.

2. The process of claim 1 wherein the solvent is pyridine or dimethylformamide.

3. The process of any one of claims 1 or 2 wherein the reaction is carried out in the presence of N-hydroxy-5-norbornene-2,3-dicarboximide and N-ethylmorpholine in addition to dicyclohexylcarbodiimide.

4. The process of claim 1 wherein the glycolic acid is HO$^{13}$CH$_2$$^{13}$COOH and a reaction product is

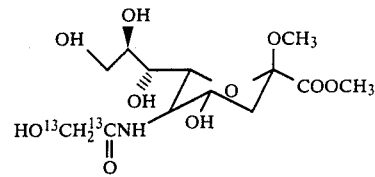

5. The process of claim 4 wherein the solvent is pyridine or dimethylformamide.

6. The process of any one of claims 4 or 5 wherein the reaction is carried out in the presence of N-hydroxy-5-norbornene-2,3-dicarboximide and N-ethylmorpholine in addition to dicyclohexylcarbodiimide.

* * * * *